(12) United States Patent
Syvret et al.

(10) Patent No.: US 7,339,081 B2
(45) Date of Patent: Mar. 4, 2008

(54) ROUTE TO PREPARE 4-BROMO-1-OXYPENTAFLUOROSULFANYL-BENZENE

(75) Inventors: Robert George Syvret, Allentown, PA (US); Gauri Sankar Lal, Whitehall, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 71 days.

(21) Appl. No.: 11/484,226

(22) Filed: Jul. 10, 2006

(65) Prior Publication Data
US 2008/0009653 A1 Jan. 10, 2008

(51) Int. Cl.
  *C07C 315/00* (2006.01)
  *C07C 317/00* (2006.01)
  *C07C 319/00* (2006.01)
  *C07C 331/00* (2006.01)
  *C07C 381/00* (2006.01)

(52) U.S. Cl. .............................. 568/18; 568/1; 568/54; 568/56; 568/6

(58) Field of Classification Search .................. 568/18, 568/1, 54, 56, 6
See application file for complete search history.

(56) References Cited

FOREIGN PATENT DOCUMENTS

DE     100 58 472        6/2001
DE     10058472 A1  *    6/2001
GB     928412       *    6/1963

OTHER PUBLICATIONS

J.R. Case, et al, "Preparation and Properties of Some Pentafluorosulphuroxyaryl . . . ," J. Chem. Soc., 1962, pp. 2107-2110.

* cited by examiner

Primary Examiner—Yvonne (Bonnie) Eyler
Assistant Examiner—Chukwuma O. Nwaonicha
(74) Attorney, Agent, or Firm—Geoffrey L. Chase

(57) ABSTRACT

A process for preparing bromo-1-oxypentafluorosulfanylbenzene is provided, the process including the step of brominating pentafluorosulfanyloxybenzene with a bromination agent to provide the bromo-1-oxypentafluorosulfanylbenzene. The process is more effective than prior art processes for preparing such compounds.

12 Claims, No Drawings

ROUTE TO PREPARE 4-BROMO-1-OXYPENTAFLUOROSULFANYL-BENZENE

BACKGROUND OF THE INVENTION

The present invention pertains to processes for preparing 4-bromo-1-oxypentafluorosulfanylbenzene.

Aryl-OSF$_5$ compounds are useful for preparing many other useful compounds including, but not limited to, agricultural compounds, pharmaceuticals, monomers and polymers.

For example, DE 100 58 472 A1 to Kirsch et al. discloses derivatives of 4-((hetero)cyclyl)-pentafluorosulfuranyloxybenzene, which are used in liquid crystal media for LCDs and other electro-optical devices. This reference discloses that 4-bromo-l-oxypentafluorosulfanylbenzene can be prepared by reacting bromobenzene with SF$_5$OOSF$_5$ at 150° C. for 18 hours in a nickel-lined autoclave. The product is recovered by fractional distillation.

Case et al., "Preparation and Properties of Some Pentafluorosulphuroxyaryl Compounds, ArO-SF$_5$." J. Am. Chem. Soc. 2107 (1962), discloses that bispentafluorosulphur compounds react with benzene, toluene or chlorobenzene to yield compounds in which the pentafluorosulphuroxy group is substituted on the aromatic ring.

Despite the foregoing developments, it is desired to provide other routes to prepare pentafluorosulfuroxyaryl compounds, and particularly 4-bromo-1-oxypentafluorosulfanylbenzene.

All references cited herein are incorporated herein by reference in their entireties.

BRIEF SUMMARY OF THE INVENTION

Accordingly, a process for preparing bromo-1-oxypentafluorosulfanylbenzene is provided, said process comprising brominating pentafluorosulfanyloxybenzene with a bromination agent to provide the bromo-1-oxypentafluorosulfanylbenzene.

DETAILED DESCRIPTION OF THE INVENTION

The invention provides a process for preparing bromo-1-oxypentafluorosulfanylbenzene, which is much more effective than prior art processes for preparing such compounds. The most preferred product of the process is 4-bromo-1-oxypentafluorosulfanylbenzene, which has the following formula:

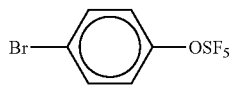

Other, less preferred, isomers of this product can also be produced in the inventive process, including 2-bromo-1-oxypentafluorosulfanylbenzene and 3-bromo-1-oxypentafluorosulfanylbenzene. In preferred embodiments of the invention, the yield of the para (i.e., 4-bromo) isomer is maximized relative to the yield of the other isomer(s). In certain embodiments of the invention, the products include the para and ortho isomers, wherein the para isomer is greater than 50% of the total amount of bromo-1-oxypentafluorosulfanylbenzene isomers. Preferably, the product mixture obtained by the process of the invention comprises more 4-bromo-1-oxypentafluorosulfanylbenzene than 2-bromo-1-oxypentafluorosulfanylbenzene. In certain embodiments, the product mixture comprises at least 51 wt% 4-bromo-1-oxypentafluorosulfanylbenzene and 0 to 49 wt% 2-bromo-1-oxypentafluorosulfanylbenzene.

The inventive process uses pentafluorosulfanyloxybenzene as a reagent. Pentafluorosulfanyloxybenzene, has the following formula:

Means for providing pentafluorosulfanyloxybenzene for use in the process are not particularly limited. For example, it can be provided by the process described in Case et al., cited above. Thus, a bispentafluorosulphur compound can be reacted with benzene to yield pentafluorosulfanyloxybenzene. Suitable bispentafluorosulphur compounds may include, but are not limited to, SF$_5$OOSF$_5$, SF$_5$OOCF$_3$, SF$_5$OOTeF$_5$, SF$_5$OOSO$_2$F, SF$_5$OSF$_5$, S$_2$F$_{10}$, or SF$_5$OX (where X =F or Cl).

The pentafluorosulfanyloxybenzene forming reaction is optionally conducted in a radical-tolerant solvent, such as, e.g., FREON F-113 or CCl$_4$.

In certain embodiments of the pentafluorosulfanyloxybenzene-providing reaction, the reaction mixture is heated to about 50 to 150° C. (preferably about 125° C.) and stirred at temperature for 10-25 hours, preferably about 18 hours. After the specified time, the reaction product is cooled, and combined with a basic aqueous solution (preferably cold 20% aqueous KOH) such that the immiscible denser liquid portion (product) can be separated by decantation.

The reactants in the preferred pentafluorosulfanyloxybenzene-providing reaction (i.e., the bispentafluorosulphur compound and benzene) can be provided in amounts that are stoichiometrically equivalent, or substantially stoichiometrically equivalent (i.e., ±10% of precise stoichiometric equivalence). Alternatively, benzene can be provided in stoichiometric excess of the bispentafluorosulphur compound, or vice versa.

The pentafluorosulfanyloxybenzene is brominated with a bromination agent to provide the desired bromo-1-oxypentafluorosulfanylbenzene. Suitable bromination agents include but are not limited to 1,3-dibromo-5,5-dimethylhydantoin, N-bromosuccinimide, N-bromoacetamide, and bromine. The most preferred bromination agents are 1,3-dibromo-5,5-dimethylhydantoin and N-bromosuccinimide.

In its simplest form, the brominating step comprises combining the pentafluorosulfanyloxybenzene and the bromination agent. In a preferred embodiment, the brominating step comprises the sequential steps of: (a) adding the bromination agent to a vessel; (b) adding to the vessel a solution comprising the pentafluorosulfanyloxybenzene in a solvent; and (c) adding a catalyst to the vessel.

The reactants (i.e., the pentafluorosulfanyloxybenzene and the bromination agent) can be provided in amounts that are stoichiometrically equivalent, or substantially stoichiometrically equivalent (i.e., ±10% of precise stoichiometric equivalence). Alternatively, pentafluorosulfanyloxybenzene can be provided in stoichiometric excess of the bromination agent, or vice versa.

In certain embodiments, the molar ratio of the pentafluorosulfanyloxybenzene to bromine of the bromination agent is from 1:2 to 2:1 or 1:1.05 to 1.05:1.

The solvent is preferably an organic solvent, more preferably a non-polar organic solvent, and most preferably methylene chloride. Other solvents suitable for use in the brominating step include but are not limited to $CHCl_3$, $CCl_4$, $CH_3CN$, THF, and other hydrocarbon solvents.

The catalyst for the brominating step is preferably triflic acid. Other suitable catalysts include but are not limited to acetic, trifluoroacetic, sulfuric, and fluorosulfonic (fluorosulfuric) acids. The catalyst is preferably provided in an amount of 5 mol% to 100 mol % relative to the brominating agent.

The yield of bromo-1-oxypentafluorosulfanylbenzene from the inventive process is preferably at least 75% of a theoretical yield, more preferably at least 90%, and still more preferably at least 95%.

EXAMPLES

The invention will be illustrated in more detail with reference to the following Examples, but it should be understood that the present invention is not deemed to be limited thereto.

Example 1

Preparation of $C_6H_5OSF_5$ (Excess $C_6H_6$, no solvent)

Into a 50-cc stirred reactor (Parr Instrument Co.) were loaded 21.75 g (76.0 mmol) $SF_5OOSF_5$ and 11.95 g $C_6H_6$ (153 mmol). The mixture was heated to 125° C. and stirred at temperature for about 18 hours. After the specified time, the reactor and contents were cooled and vented. The reaction product was poured into a beaker containing cold 20% aqueous KOH and the immiscible denser liquid portion (product) was separated by decantation. Analysis of the product by GC-MS revealed a product distribution (normalized) containing residual benzene ($C_6H_6$ =37.5%), fluorobenzene ($C_6H_5F$ =9.2 %), oxypentafluorosulfanyl benzene ($C_6H_5OSF_5$=50.1%), oxypentafluorosulfanylfluorobenzene ($C_6H_4FOSF_5$ =0.9 %), bis(oxypentafluorosulfanyl)benzene ($C_6H_4(OSF_5)_2$ =2.3%) as well as other minor products.

Example 2

Preparation of $C_6H_5OSF_5$ (Near-stoichiometric $C_6H_6$, no solvent)

Into a 50-cc stirred reactor (Parr Instrument Co.) were loaded 23.02 g (80.5 mmol) $SF_5OOSF_5$ and 6.41 g $C_6H_6$ (82.1 mmol). The mixture was heated to 124° C. and stirred at temperature for about 4 hours. After the specified time, the reactor and contents were cooled and vented. The reaction product was poured into a beaker containing cold water and subsequently neutralized with aqueous bicarbonate. The product was extracted into $CH_2Cl_2$ and separated by decantation. Analysis of the product by GC-MS revealed a product distribution (normalized) containing residual benzene ($C_6H_6$ =29.8%), fluorobenzene ($C_6H_5F$ =6.4%), oxypentafluorosulfanyl benzene ($C_6H_5OSF_5$ =57.7%), oxypentafluorosulfanylfluorobenzene ($C_6H_4FOSF_5$ =3.6 %), bis(oxypentafluorosulfanyl)benzene ($C_6H_4(OSF_5)_2$ =2.5%) as well as other minor products.

Example 3

Preparation of $C_6H_5OSF_5$ (Stoichiometric $C_6H_6$, no solvent)

The method of Example 2 was repeated, with 25.07 g (87.6 mmol) $SF_5OOSF_5$ and 6.85 g (87.7 mmol) $C_6H_6$ heated to 125° C. for 5 hours. Analysis by GC-MS after workup revealed a product distribution (normalized) containing residual benzene ($C_6H_6$ =25.0%), fluorobenzene ($C_6H_5F$ = 10.3%), oxypentafluorosulfanyl benzene ($C_6H_5OSF_5$ =50.0 %), oxypentafluorosulfanylfluorobenzene ($C_6H_4FOSF_5$ =9.5 %), bis(oxypentafluorosulfanyl)benzene ($C_6H_4(OSF_5)_2$ =5.3 %) as well as other minor products.

Example 4

Preparation of $C_6H_5OSF_5$ (Near-stoichiometric $C_6H_6$, F-113 solvent)

Into a 50-cc stirred reactor (Parr Instrument Co.) were loaded 14.9 g (52.1 mmol) $SF_5OOSF_5$, 4.5 g $C_6H_6$ (57.6 mmol), and 20 mL Freon®-113 (F-113). The mixture was heated to 150 ° C. and stirred at temperature for about 15 hours. After the specified time, the reactor and contents were cooled and vented. The reaction product was poured into a beaker containing cold 20% aqueous KOH and the immiscible denser liquid portion (product) was separated by decantation. Analysis of the product by GC-MS revealed a product distribution (normalized) containing residual benzene ($C_6H_6$ =52.5%), fluorobenzene ($C_6H_5F$ =10.0%), oxypentafluorosulfanyl benzene ($C_6H_5OSF_5$ =33.6%), oxypentafluorosulfanylfluorobenzene ($C_6H_4FOSF_5$ =2.9%), bis(oxypentafluorosulfanyl)benzene ($C_6H_4(OSF_5)_2$ =1.0%) as well as other minor products.

Example 5

Preparation of bromo-1-oxypentafluorosulfanylbenzene, $BrC_6H_4OSF_5$

A 50 mL 3-neck round bottom flask equipped with a rubber septum, $N_2$ inlet tube, glass stopper and magnetic stir bar was charged with 1,3-dibromo-5,5- dimethylhydantoin (1.741 g, 6.075 mmol) under $N_2$ and cooled to 0° C. A solution of pentafluorosulfanyloxy benzene, $PhOSF_5$ (2.70g, 12.15 mmol) in $CH_2Cl_2$ (27 mL) was added followed by triflic acid (1.08 mL). The reaction was monitored by GC-MS for disappearance of starting material. After 30 min the mixture was treated with saturated $NaHCO_3$. After $CO_2$ evolution ceased, the $CH_2Cl_2$ solution was separated, dried ($MgSO_4$), filtered and evaporated in vacuo. The residue was purified by adsorption on a silica gel plug (10 g) and eluting with EtOAc/Hexane (98:2 ratio) to obtain 3.46 g (95% yield) of bromo-1-oxypentafluorosulfanylbenzene. Major isomer: 4-bromo-1-oxypentafluorosulfanylbenzene; GC-MS m/e = 300($M^+$), $^1H$ NMR ($CDCl_3$) δ 7.55 (d, 2H), 7.15 (d, 2H). $^{19}F$ NMR ($CDCl_3$) δ 72 (q, 1F), 62 (d, 4F). Minor isomer: 2-bromo-1-oxypentafluorosulfanylbenzene: GC-MS m/e = 300($M^+$); 'H NMR ($CDCl_3$) δ 7.65 (d, 1 H), 7.40 (d, 1 H), 7.35 (br. s, 2H); $^{19}F$ NMR ($CDCl_3$) δ72 (q, 1 F), 64 (d, 4 F).

Example 6

The procedure of Example 5 was carried out with $PhOSF_5$ (200 mg, 0.9 mmol) and N-bromosuccinimide (160 mg, 0.9 mmol) in $CH_2Cl_2$ (2.0 mL) and triflic acid (80 μL) for 30 min at 0° C. Work up as above afforded 251 mg (93% yield) of bromo-1-oxypentafluorosulfanylbenzene with isomer ratio similar to that from the reaction described in Example 5.

COMPARATIVE EXAMPLES

A series of Comparative Examples (Examples 7-11) were done to demonstrate the inferiority of reacting bromobenzene with $SF_5OOSF_5$ (as suggested by DE 100 58 472 A1) to obtain 4-bromo-phenyl-$OSF_5$.

Comparative Example 7

Reaction of $C_6H_5Br$ with $SF_5OOSF_5$ without solvent at 125° C. for 62 hours Into a 50-cc reactor (Parr Instrument Co.) were loaded 6.6 g (23.1 mmol) $SF_5OOSF_5$ and 3.7 g $C_6H_5Br$ (23.6 mmol). The mixture was heated to 125° C. and held at temperature for about 62 hours. After the specified time, the reactor and contents were cooled and vented. The reaction product was poured into a beaker containing cold water and subsequently neutralized with aqueous bicarbonate. The product was extracted into $CH_2Cl_2$ and separated by decantation. Analysis of the product by GC-MS revealed a normalized product distribution as follows:

TABLE 1

Normalized Area % Results for Example 7.

| Product | GC Area | Normalized Area % |
|---|---|---|
| $C_6H_5Br$ | 130317890 | 23.8% |
| $C_6H_4BrF$ | 11322510 | 2.1% |
| $C_6H_3Br_2F$ | 7151299 | 1.3% |
| $C_6H_3FBrOSF_5$ (isomer a) | 1908926 | 0.3% |
| $C_6H_3FBrOSF_5$ (isomer b) | 4963476 | 0.9% |
| $C_6H_3FBrOSF_5$ (isomer c) | 1483302 | 0.3% |
| $C_6H_4BrOSF_5$ (isomer 1) | 45896673 | 8.4% |
| $C_6H_4BrOSF_5$ (isomer 2) | 142391610 | 26.0% |
| $C_6H_4BrOSF_5$ (isomer 3) | 71123345 | 13.0% |
| $C_6H_4Br_2$ | 61429450 | 11.2% |
| $C_6H_4Br_2$ | 25598132 | 4.7% |
| $C_6H_4(OSF_5)_2$ | 42108451 | 7.7% |
| $C_6H_4(OSF_5)_2$ | 2031913 | 0.4% |

Comparative Example 8

Reaction of $C_6H_5Br$ with $SF_5OOSF_5$ without solvent at 150° C. for 4 hours

Into a 50-cc reactor (Parr Instrument Co.) were loaded 5.4 g (18.9 mmol) $SF_5OOSF_5$ and 2.5 g $C_6H_5Br$ (15.9 mmol). The mixture was heated to 150° C. and held at temperature for about 4 hours. After the specified time, the reactor and contents were cooled and vented. The product was extracted into $CH_2Cl_2$ and separated by decantation. Analysis of the product by GC-MS revealed a normalized product distribution as follows:

TABLE 2

Normalized Area % Results for Example 8.

| Product | GC Area | Normalized Area % |
|---|---|---|
| $C_6H_5Br$ | 175126741 | 46.9% |
| $C_6H_4BrF$ (isomer i) | 12731248 | 3.4% |
| $C_6H_4BrF$ (isomer ii) | 5688453 | 1.5% |

TABLE 2-continued

Normalized Area % Results for Example 8.

| Product | GC Area | Normalized Area % |
|---|---|---|
| $C_6H_3FBrOSF_5$ (isomer a) | 497408 | 0.1% |
| $C_6H_3FBrOSF_5$ (isomer b) | 220192 | 0.1% |
| $C_6H_3FBrOSF_5$ (isomer c) | 1007588 | 0.3% |
| $C_6H_4BrOSF_5$ (isomer 1) | 15827801 | 4.2% |
| $C_6H_4BrOSF_5$ (isomer 2) | 55554072 | 14.9% |
| $C_6H_4BrOSF_5$ (isomer 3) | 28544473 | 7.6% |
| $C_6H_4Br_2$ | 43407648 | 11.6% |
| $C_6H_4Br_2$ | 16520858 | 4.4% |
| $C_6H_4(OSF_5)_2$ | 18031721 | 4.8% |
| $C_6H_4(OSF_5)_2$ | 420381 | 0.1% |

Comparative Example 9

Reaction of $C_6H_5Br$ with $SF_5OOSF_5$ without solvent at 100° C. for 17 hours Into a 50-cc reactor (Parr Instrument Co.) were loaded 6.4 g (22.4 mmol) $SF_5OOSF_5$ and 5.2 g $C_6H_5Br$ (33.1 mmol). The mixture was heated to 100° C. and stirred at temperature for about 17 hours. After the specified time, analysis of the product by GC-MS revealed a normalized product distribution as follows:

TABLE 3

Normalized Area % Results for Example 9.

| Product | GC Area | Normalized Area % |
|---|---|---|
| $C_6H_5Br$ | 102914338 | 23.0% |
| $C_6H_4BrF$ (all isomers) | 5668030 | 1.3% |
| $C_6H_3FBrOSF_5$ (all isomers) | 11732015 | 2.6% |
| $C_6H_4BrOSF_5$ (all isomers) | 289983915 | 64.7% |
| $C_6H_4Br_2$ (all isomers) | 25008815 | 5.6% |
| $C_6H_4(OSF_5)_2$ (all isomers) | 12741470 | 2.8% |

Comparative Example 10

Reaction of $C_6H_5Br$ with $SF_5OOSF_5$ in $CH_2Cl_2$ solvent at 150° C. for 22 hours Into a 50-cc reactor (Parr Instrument Co.) were loaded 4.8 g (16.8 mmol) $SF_5OOSF_5$, 2.8 g $C_6H_5Br$ (17.8 mmol), and 20 mL $CH_2Cl_2$. The mixture was heated to 150° C. and stirred at temperature for about 22 hours. After the specified time, the reactor and contents were cooled and vented. The product was extracted into $CH_2Cl_2$ and separated by decantation. Analysis of the product by GC-MS revealed a normalized product distribution as follows:

TABLE 4

Normalized Area % Results for Example 10.

| Product | GC Area | Normalized Area % |
|---|---|---|
| $C_6H_5Br$ | 57955908 | 34.3% |
| $C_6H_4BrF$ (all isomers) | 3899930 | 2.3% |
| $C_6H_4BrClOSF_5$ (all isomers) | 20912871 | 12.4% |
| $C_6H_4BrOSF_5$ (all isomers) | 7882943700 | 46.6% |

TABLE 4-continued

Normalized Area % Results for Example 10.

| Product | GC Area | Normalized Area % |
|---|---|---|
| $C_6H_4Br_2$ (all isomers) | 3104083 | 1.8% |
| $C_6H_4(OSF_5)_2$ (all isomers) | 4452776 | 2.6% |

Comparative Example 11

Reaction of $C_6H_5Br$ with $SF_5OOSF_5$ in F-113 solvent at 125° C. for 14 hours Part 1: Heating at 125° C. for 14 hours Into a 50-cc reactor (Parr Instrument Co.) were loaded 18.6 g (65.0 mmol) $SF_5OOSF_5$, 10.4 g $C_6H_5Br$ (66.2 mmol), and 30 mL F-113 solvent. The mixture was heated to 125° C. and stirred at temperature for about 14 hours. After the specified time, the reactor and contents were cooled and vented. Analysis of the product by GC-MS revealed a normalized product distribution given in the first column of the Table 5.

Part 2: Heating at 125° C. for additional 14 hours

The reactor and contents were reheated to 125° C. and maintained there for an additional 14 hours. After the specified time, the reactor and contents were cooled and vented. Analysis of the product by GC-MS revealed a normalized product distribution given in the second column of the Table 5.

Part 3: Heating at 150° C. for additional 15 hours

The reactor and contents were reheated to 150° C. and maintained there for an additional 15 hours. After the specified time, the reactor and contents were cooled and vented. Analysis of the product by GC-MS revealed a normalized product distribution given in the third column of the Table 5.

TABLE 5

Normalized Area % Results for Example 11 Parts 1-3.

| Product | Example 11 Part 1 Normalized Area % | Example 11 Part 2 Normalized Area % | Example 11 Part 3 Normalized Area % |
|---|---|---|---|
| $C_6H_5Br$ | 50.3% | 46.4% | 29.4% |
| $C_6H_4BrF$ (all isomers) | 2.4% | 4.6% | 7.4% |
| $C_6H_4BrFOSF_5$ (all isomers) | 0.9% | 2.1% | 2.1% |
| $C_6H_4BrOSF_5$ (all isomers) | 18.0% | 19.8% | 26.6% |
| $C_6H_4Br_2$ (all isomers) | 20.2% | 20.0% | 24.2% |
| $C_6H_3Br_2F$ | 3.9% | 2.1% | 1.6% |
| $C_6H_4(OSF_5)_2$ (all isomers) | 4.3% | 5.0% | 8.7% |

TABLE 6

Summary of Comparative Examples 7-11.

| Example Number | Conversion of $C_6H_5Br$ to Products | Total Amount of Br-Ph-$OSF_5$ (3 isomers) Obtained |
|---|---|---|
| 7 | 76.2% | 47.4% |
| 8 | 53.1 % | 26.7% |
| 9 | 77.0 % | 64.7% |
| 10 | 65.7% | 46.6% |
| 11 | 70.6% | 26.6% |

The Examples showed that the method described in DE 10058472 A1 is far inferior to the method of the invention.

While the invention has been described in detail and with reference to specific examples thereof, it will be apparent to one skilled in the art that various changes and modifications can be made therein without departing from the spirit and scope thereof.

The invention claimed is:

1. A process for preparing bromo-1-oxypentafluorosulfanylbenzene, the process comprising brominating pentafluorosulfanyloxybenzene with a bromination agent to provide the bromo-1-oxypentafluorosulfanylbenzene.

2. The process of claim 1, wherein the bromination agent is at least one member selected from the group consisting of 1,3-dibromo-5,5-dimethylhydantoin, N-bromosuccinimide, N-bromoacetamide and bromine.

3. The process of claim 1, wherein the brominating step comprises mixing the pentafluorosulfanyloxybenzene, the bromination agent and a catalyst in a non-polar organic solvent.

4. The process of claim 1, wherein the brominating comprises the sequential steps of: (a) adding the bromination agent to a vessel; (b) adding to the vessel a solution comprising the pentafluorosulfanyloxybenzene in a non-polar organic solvent; and (c) adding a catalyst to the vessel.

5. The process of claim 4, wherein the catalyst is triflic acid.

6. The process of claim 5, wherein the bromination agent is 1,3-dibromo-5,5-dimethylhydantoin or N-bromosuccinimide.

7. The process of claim 6, wherein the solvent is methylene chloride.

8. The process of claim 7, wherein a molar ratio of the pentafluorosulfanyloxybenzene to bromine of the bromination agent is from 1:2 to 2:1.

9. The process of claim 8, wherein the molar ratio is 1:1.05 to 1.05:1.

10. The process of claim 1, wherein the bromo-1-oxypentafluorosulfanylbenzene is provided in a product mixture comprising at least one of 4-bromo-1-oxypentafluorosulfanylbenzene and 2-bromo-1-oxypentafluorosulfanylbenzene.

11. The process of claim 10, wherein the product mixture comprises more 4-bromo-1-oxypentafluorosulfanylbenzene than 2-bromo-1-oxypentafluorosulfanylbenzene.

12. The process of claim 10, wherein the product mixture comprises at least 51 wt % 4-bromo-1-oxypentafluorosulfanylbenzene and 0 to 49 wt % 2-bromo-1-oxypentafluorosulfanylbenzene.

* * * * *

UNITED STATES PATENT AND TRADEMARK OFFICE
CERTIFICATE OF CORRECTION

PATENT NO. : 7,339,081 B2  Page 1 of 1
APPLICATION NO. : 11/484226
DATED : March 4, 2008
INVENTOR(S) : Robert George Syvret and Gauri Sankar Lal It is certified that error appears in the above-identified patent and that said Letters Patent is hereby corrected as shown below:

Column 8, Line 62

In claim 12 delete the number "10" and insert the number -- 11 --

Signed and Sealed this

Eighth Day of April, 2008

JON W. DUDAS
*Director of the United States Patent and Trademark Office*